US010722659B2

(12) United States Patent
Cox et al.

(10) Patent No.: US 10,722,659 B2
(45) Date of Patent: Jul. 28, 2020

(54) APPARATUS FOR UNSHEATHING AND RESHEATHING A NEEDLE DEVICE

(71) Applicant: SOUTHERN INNOVATIONZ LIMITED, Christchurch (NZ)

(72) Inventors: Timothy Stephen Cox, Christchurch (NZ); Melissa Ann Brown, Christchurch (NZ)

(73) Assignee: SOUTHERN INNOVATIONZ LIMITED, Christchurch (NZ)

( * ) Notice: Subject to any disclaimer, the term of this patent is extended or adjusted under 35 U.S.C. 154(b) by 486 days.

(21) Appl. No.: 15/562,844

(22) PCT Filed: Mar. 29, 2016

(86) PCT No.: PCT/NZ2016/050049
§ 371 (c)(1),
(2) Date: Sep. 28, 2017

(87) PCT Pub. No.: WO2016/159782
PCT Pub. Date: Oct. 6, 2016

(65) Prior Publication Data
US 2018/0280625 A1  Oct. 4, 2018

(30) Foreign Application Priority Data
Mar. 31, 2015  (NZ) ........................... 706521

(51) Int. Cl.
*A61M 5/32*  (2006.01)
(52) U.S. Cl.
CPC ........ *A61M 5/3204* (2013.01); *A61M 5/3213* (2013.01); *A61M 2005/3215* (2013.01)
(58) Field of Classification Search
CPC .............. A61M 5/3204; A61M 5/3213; A61M 2005/3215
See application file for complete search history.

(56) References Cited

U.S. PATENT DOCUMENTS 3,012,811 A * 12/1961 Sandrock ............... G21C 19/10
294/110.1
3,205,863 A  9/1965 Rhoades
(Continued)

FOREIGN PATENT DOCUMENTS

AU  2009202158 A1  12/2009
CN  101184981 A  5/2008
(Continued)

OTHER PUBLICATIONS

International Preliminary Report on Patentability issued in PCT/NZ2016/050049 dated Oct. 3, 2017.
(Continued)

*Primary Examiner* — Laura A Bouchelle
*Assistant Examiner* — John A Doubrava
(74) *Attorney, Agent, or Firm* — Arent Fox LLP

(57) ABSTRACT

An apparatus for unsheathing and resheathing a needle device. The apparatus has a housing, a cam member that is movable in an axial direction relative to the housing, a ratchet member that is rotatable relative to the housing and movable in the axial direction between a first position and a second position upon movement of the cam member, and a clamp having at least two jaw members, configured to receive at least a portion of a needle sheath. In the first position of the ratchet member, the jaw members are in an open configuration for receipt or release of the needle sheath, and in the second position of the ratchet member, the ratchet member and/or the cam member holds the jaw members in a gripping position for gripping the needle sheath.

18 Claims, 10 Drawing Sheets

(56) References Cited

U.S. PATENT DOCUMENTS

| | | | |
|---|---|---|---|
| 4,717,386 A | | 1/1988 | Simmons |
| 4,955,865 A | | 9/1990 | Steiner et al. |
| 4,995,871 A | | 2/1991 | Sasaki et al. |
| 5,067,949 A | | 11/1991 | Freundlich et al. |
| 5,078,695 A | | 1/1992 | Farrar, Jr. et al. |
| 5,242,426 A | * | 9/1993 | Pituch ................. A61M 5/3213 206/365 |
| 5,308,582 A | * | 5/1994 | Serra ................... A61M 5/3213 269/239 |
| 5,356,385 A | | 10/1994 | Latini |
| 5,586,976 A | | 12/1996 | Coutoumanos |
| 6,065,791 A | * | 5/2000 | Anders ............... B25J 15/0206 294/116 |
| 2006/0258991 A1 | | 11/2006 | Lin |
| 2008/0210890 A1 | * | 9/2008 | Fago ................... A61M 5/1785 250/506.1 |
| 2009/0014462 A1 | * | 1/2009 | Costa ................. A61M 5/3205 221/185 |

FOREIGN PATENT DOCUMENTS

| | | |
|---|---|---|
| CN | 104053468 B | 8/2016 |
| EP | 2 295 099 A1 | 3/2011 |

OTHER PUBLICATIONS

Written Opinion issued in PCT/NZ2016/050049 dated Oct. 5, 2016.
European Search Report dated Sep. 21, 2018 issued in European Application No. EP16773537.2.
International Search Report issued in International Patent Application No. PCT/NZ2016/050049.

* cited by examiner

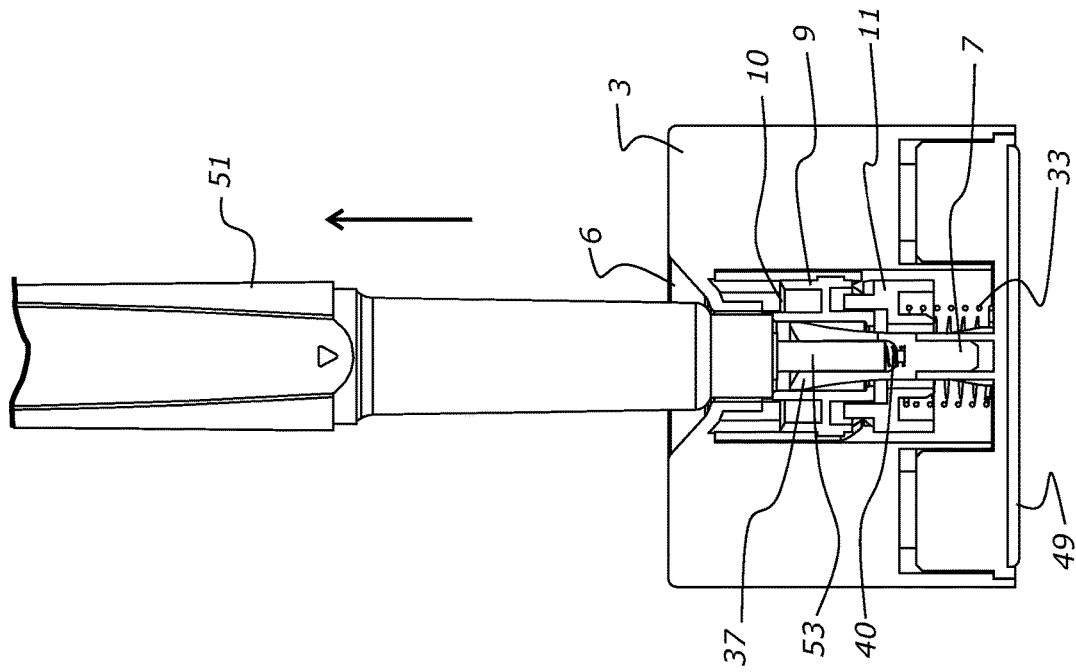
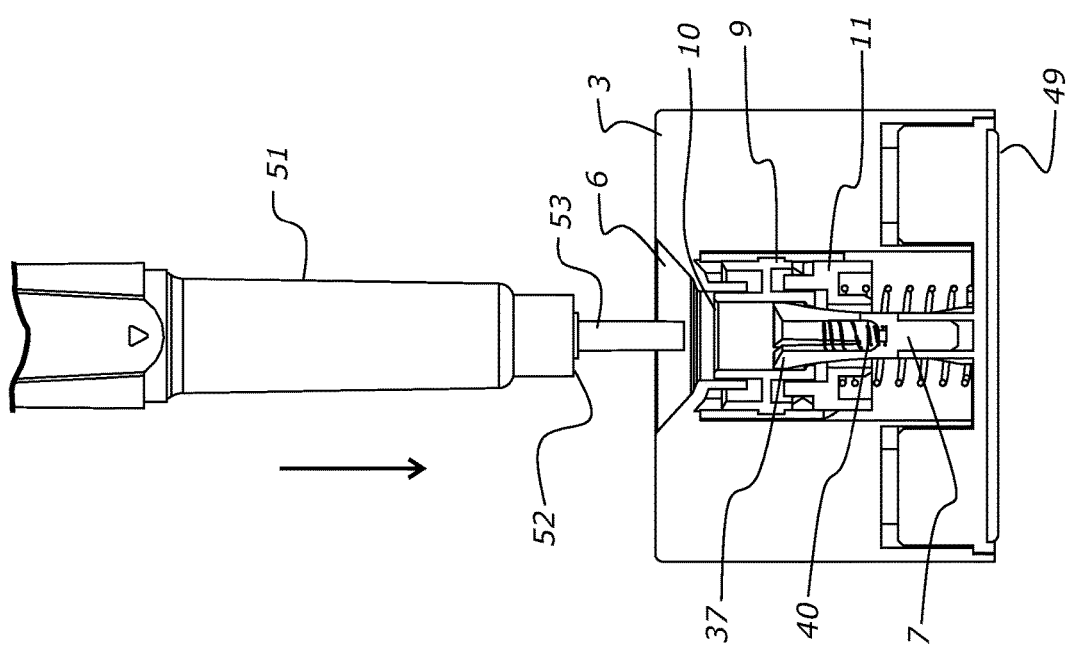
FIGURE 10(i)
FIGURE 10(ii)

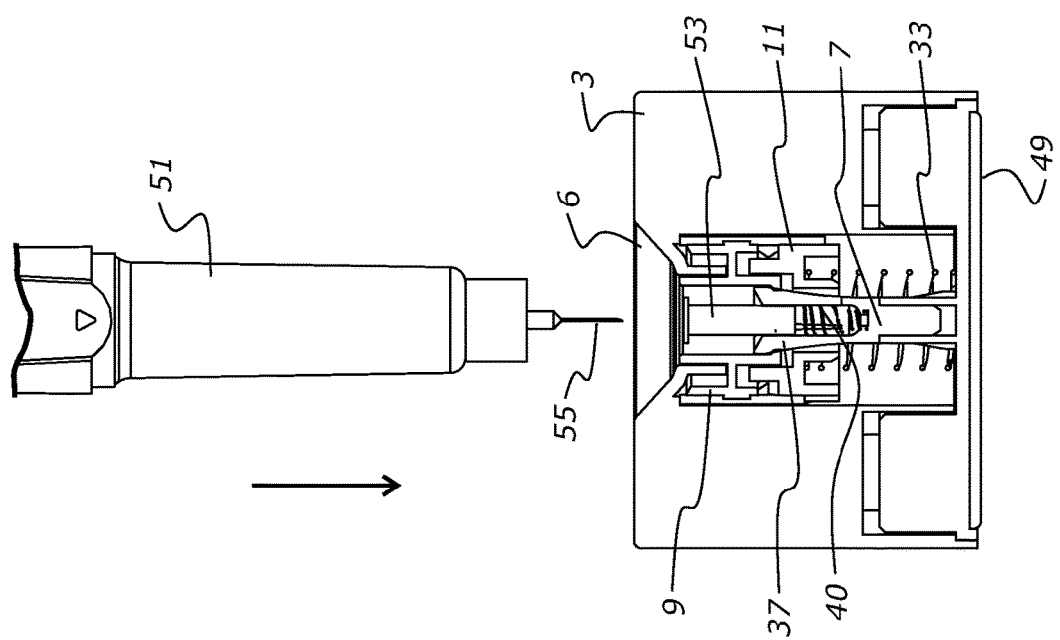
*FIGURE 10(iii)*

APPARATUS FOR UNSHEATHING AND RESHEATHING A NEEDLE DEVICE

CROSS REFERENCE TO RELATED APPLICATION

This application is a National Stage entry of International Application No.: PCT/NZ2016/050049, filed Mar. 29, 2916, which claims priority to New Zealand Patent Application No. 706521, filed Mar. 31, 2015. The disclosure of the prior applications is hereby incorporated by reference herein their entirety.

FIELD OF THE INVENTION

This invention relates to an apparatus for unsheathing and resheathing a needle device.

BACKGROUND

Removing and replacing sheaths on needles is typically a two-handed operation with the sheath being held in one hand and the needle syringe being held in the other hand, and requires careful motor control.

Requiring the use of two-hands to remove or replace a needle sheath can be disadvantageous, particularly for medical personnel who may need to also hold a patient or other medical implements. In addition, there is a high risk of a user accidentally pricking themselves with the needle if the sheath and the needle are not correctly aligned. This risk is exacerbated for people with conditions that lessen their motor control in one or both of their hands.

For example, people with diabetes commonly need to self inject insulin. However, people with diabetes commonly suffer from diabetes-related neurological conditions that may impair sensory function and/or motor function in their hands. Similarly, conditions such as arthritis or poor vision can make safely unsheathing or resheathing a needle difficult.

Some devices have been proposed to assist with unsheathing and/or resheathing needles. However, these devices have not been widely adopted, particularly outside of clinical use. Some such devices are complex with a large number of parts, and many still require two-handed operation.

It is an object of at least preferred embodiments of the present invention to address or mitigate at least one of the above mentioned disadvantages and/or to at least provide the public with a useful alternative.

In this specification where reference has been made to patent specifications, other external documents, or other sources of information, this is generally for the purpose of providing a context for discussing the features of the invention. Unless specifically stated otherwise, reference to such external documents or such sources of information is not to be construed as an admission that such documents or such sources of information, in any jurisdiction, are prior art or form part of the common general knowledge in the art.

SUMMARY OF THE INVENTION

A first aspect of the present invention provides an apparatus for unsheathing and resheathing a needle device comprising: a housing, a cam member that is movable in an axial direction relative to the housing, a ratchet member that is rotatable relative to the housing and movable in the axial direction between a first position and a second position upon movement of the cam member, and a clamp having at least two jaw members, configured to receive at least a portion of a needle sheath. In the first position of the ratchet member, the jaw members are in an open configuration for receipt or release of the needle sheath, and in the second position of the ratchet member, the ratchet member and/or the cam member holds the jaw members in a gripping position for gripping the needle sheath.

In an embodiment, the cam member is movable relative to the clamp in the axial direction, and wherein in the gripping position of the clamp, an inner surface of the cam member holds the jaw members inwards.

A second aspect of the present invention provides an apparatus for unsheathing and resheathing a needle device comprising: a housing, a clamp having at least two jaw members configured to receive at least a portion of a needle sheath, a collar positioned around the clamp and movable in the axial direction relative to the clamp and the housing between a first position and a second position, and an indexed push mechanism for moving the collar between the first and second positions upon application of a push force by the needle device. In the first collar position, the jaw members are in an open configuration for receipt or release of the needle sheath, and in the second collar position, the collar holds the jaw members inwards for gripping the needle sheath.

The collar is preferably provided by the indexed push mechanism. The indexed push mechanism may comprise a cam member that is movable in an axial direction relative to the housing and a ratchet member that is movable in the axial direction and rotatable relative to the cam member upon movement of the cam member. The collar may be provided by the cam member and/or the ratchet member.

In embodiments of the first and/or second aspects, the clamp is configured to apply a radial clamping force. For example, the clamp is preferably a radial clamp.

In an embodiment, the jaw members define a recess for receiving the needle sheath, and a biasing device is provided at the base of the recess for biasing the needle sheath away from the base of the recess.

In an embodiment, the cam member and ratchet member each comprise a collar, and the collars extend around a portion of the clamp. The collars may receive the needle sheath. Preferably, the cam member collar and ratchet member collar are coaxial.

In an embodiment, the ratchet member is biased in the axial direction, toward an aperture in the housing for receipt of the needle sheath. For example, the ratchet member may be biased upwards relative to a base of the housing, in a direction away from the base of the housing. The ratchet member may comprise a plurality of angled primary teeth, with the cam member having at least one angled cam surface configured to engage the primary teeth on the cam member. Preferably, the cam member comprises a plurality of cam surfaces In an embodiment, the cam member comprises at least one guide slidably engaged with the housing. The at least one guide may comprise a plurality of projections, slidable in complementary guide grooves in a bore of the housing.

In an embodiment, the ratchet member further comprises at least one secondary tooth and the housing comprises a plurality of angled cam surfaces configured to turn the ratchet member to allow the secondary tooth to enter a complementary tooth slot in the housing. Preferably, the ratchet member comprises a plurality of secondary teeth, and the housing comprises a corresponding number of complementary tooth slots.

In the first position of the collar or ratchet member, the secondary ratchet teeth may be configured to be positioned on the angled cam surfaces on the housing; and in the second position of the collar or ratchet member, the secondary ratchet teeth may be configured to be positioned in a respective housing slot. In an embodiment, the cam surfaces and slots on the housing are configured to turn the ratchet member through 45 degrees as it moves between the first position of the collar or ratchet member and the second position of the collar or ratchet member. The ratchet member is preferably configured to be turnable in only one direction, for example anticlockwise or clockwise.

In an embodiment the clamp jaw members comprise a plurality of resilient fingers. The fingers are preferably biased to the open position and pushable inwards to the gripping position.

In an embodiment, the housing comprises an aperture for receiving the needle sheath. The aperture is preferably provided on a top side of the housing and may be chamfered to assist with placement of the sheath into the aperture. A base of the housing may be configured to rest on or affix to a surface, preferably to a horizontal surface.

The apparatuses of the first and second aspects may have any one or more features outlined in relation to the other aspect. For example, the apparatus of the first aspect may utilise an indexed push mechanism. As another example, the ratchet member and/or cam member of the first aspect may be in the form of collar(s).

A third aspect of the present invention provides a method of unsheathing a sheathed needle device comprising pressing the sheathed needle device into the apparatus described above such that the clamp grips the sheath, and lifting the needle device from the apparatus, wherein the sheath remains in the clamp.

A fourth aspect of the present invention provides a method of sheathing an unsheathed needle using the apparatus described above, wherein the clamp of the apparatus is gripping a sheath, the method comprising pressing the needle device into the sheath to attach the sheath to the needle device, and lifting the needle device from the apparatus such that the clamp releases the sheath.

The term 'comprising' as used in this specification and claims means 'consisting at least in part of'. When interpreting statements in this specification and claims which include the term 'comprising', other features besides the features prefaced by this term in each statement can also be present. Related terms such as 'comprise' and 'comprised' are to be interpreted in a similar manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

As used herein the term '(s)' following a noun means the plural and/or singular form of that noun.

As used herein the term 'and/or' means 'and' or 'or', or where the context allows both.

The invention consists in the foregoing and also envisages constructions of which the following gives examples only.

BRIEF DESCRIPTION OF THE DRAWINGS

The present invention will now be described by way of example only and with reference to the accompanying drawings in which.

DETAILED DESCRIPTION OF A PREFERRED EMBODIMENT

Figure 1:
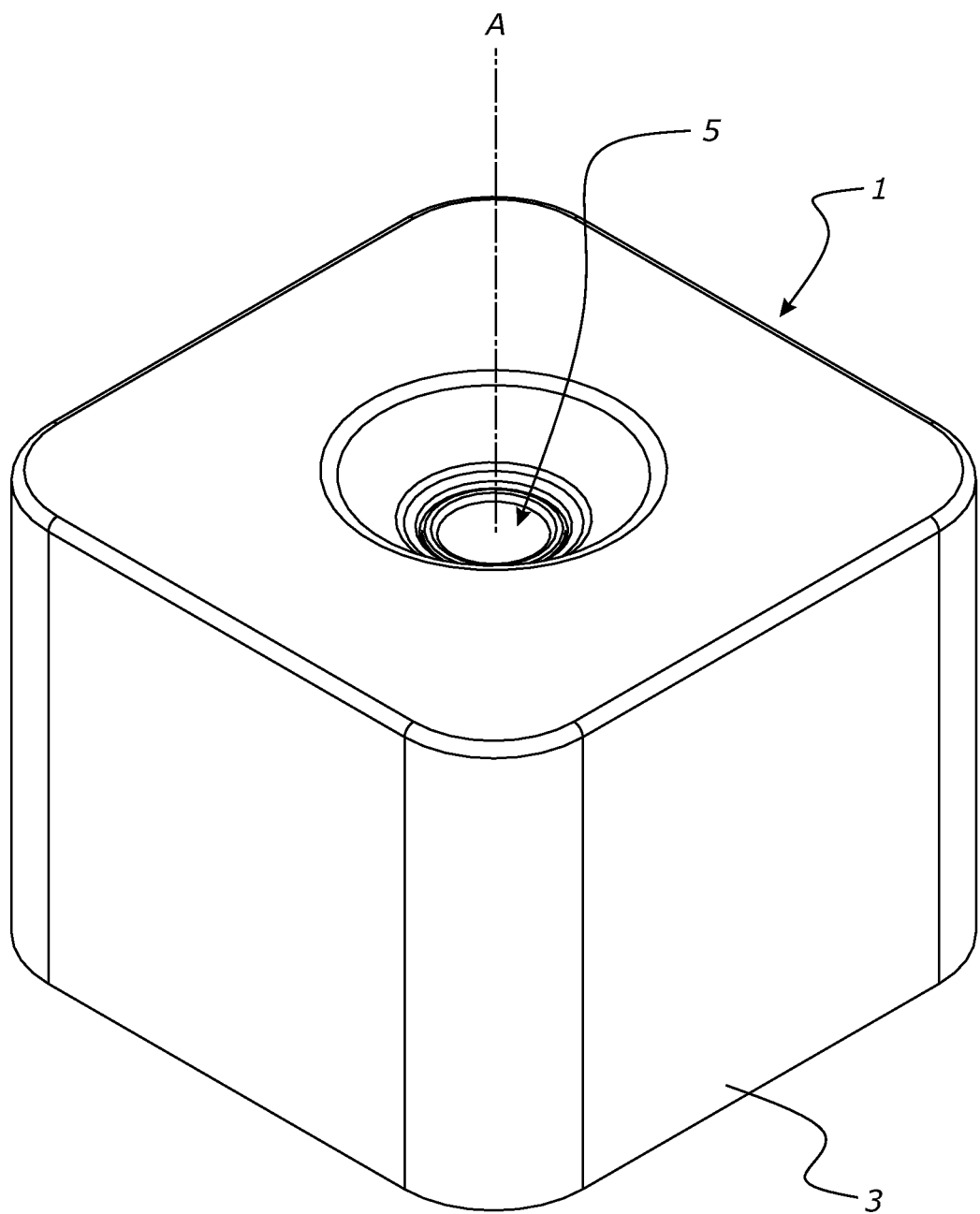
FIG. 1 is a perspective view of an exemplary apparatus according to an embodiment of the invention
Figure 2:
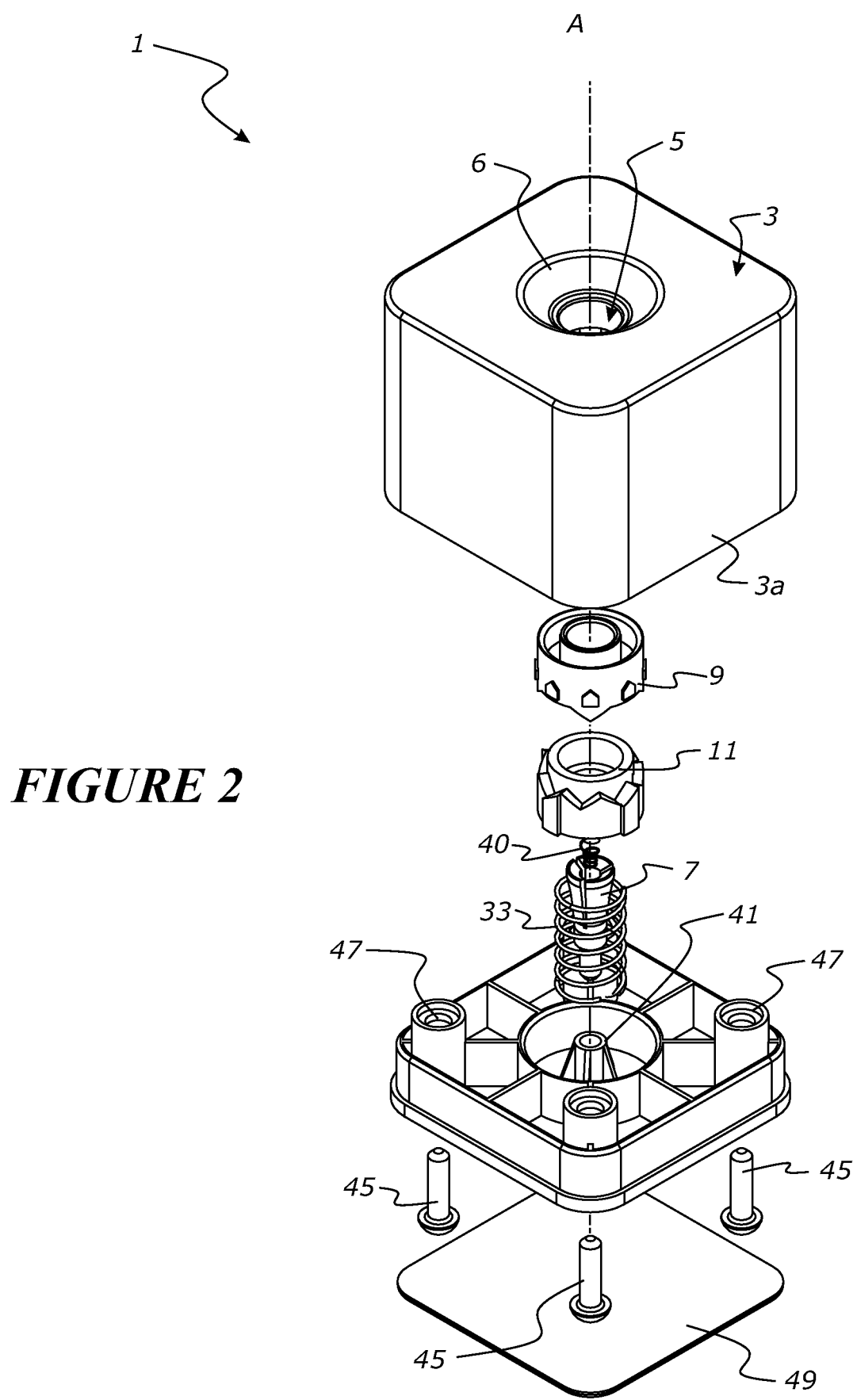
FIG. 2 is an exploded perspective view of the apparatus of FIG. 1.

FIGS. 1 to 8 show an exemplary embodiment apparatus 1 for removing the sheath from a needle of a needle device and resheathing a needle of a needle device. The apparatus 1 comprises a housing 3 that houses a radial clamp 7 and a push mechanism for opening or clamping the clamp 7 upon downward pressure of a needle sheath pushed into the apparatus 1.

The housing 3 comprises a top shell 3*a* and a base 3*b*. The top shell 3*a* has a central bore or aperture 5 for receiving the sheath or cap 53 of a needle device 51. The needle device comprises a body, needle 55, and a sheath 53.

The mechanism for opening or clamping the clamp 7 comprises a cam member 9, a ratchet member 11, and a biasing device in the form of a spring 33. The clamp 7, cam member 9, ratchet member 11, spring 33, and the housing aperture 5 are all coaxial along an axis A.

Figure 3:
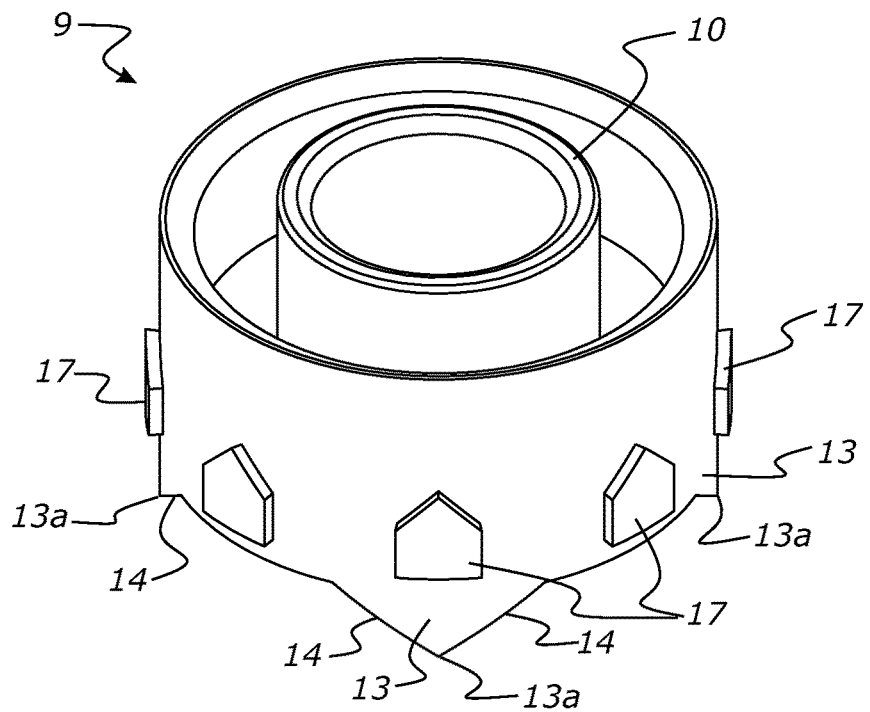
FIG. 3 is a perspective view of the cam member of the apparatus shown in FIGS. 1 and 2.

Referring to FIG. 3, the cam member 9 is ring shaped and comprises a collar with four downwards, discrete v-shaped cam projections 13 that form cam surfaces 14. The peripheral surface of the cam member 9 has eight guide projections 17.

Figure 4:
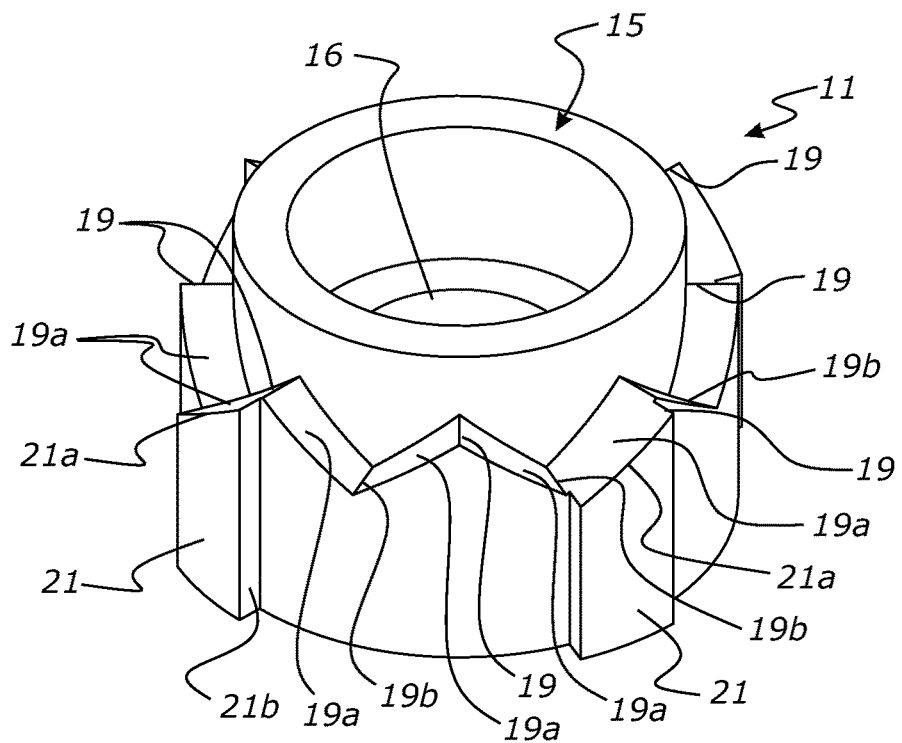
FIG. 4 is a perspective view of the ratchet member of the apparatus shown in FIGS. 1 and 2.
Figure 5:
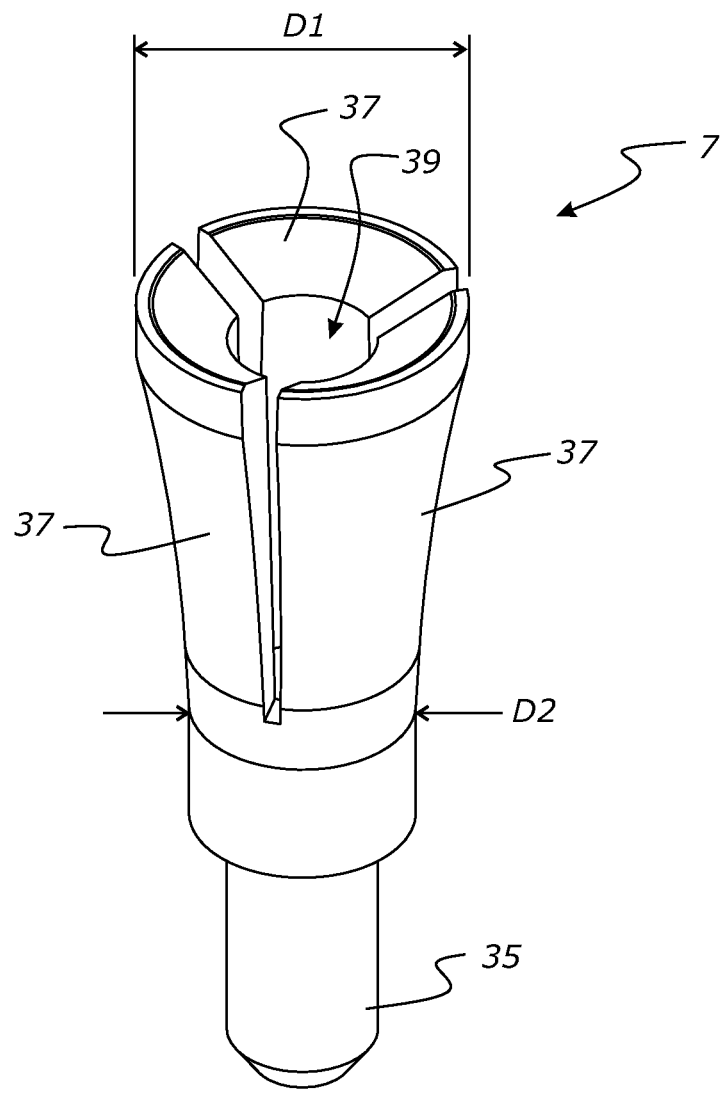
FIG. 5 is a perspective view of the radial clamp of the apparatus shown in FIG. 2.

Referring to FIG. 4, the ratchet member 11 is also a ring-shaped member comprising a collar 15. The peripheral surface of the collar 15 has eight v-shaped primary teeth 19 facing upwards. These primary teeth 19 are configured to contact the cam projections 13 on the cam member 9.

A further four discrete secondary teeth 21 project outwards from the cam member collar 15 and primary teeth 21. The secondary teeth 12 are ratchet teeth and each comprise an angled surface 21a, all angled in the same direction, and a substantially vertical surface 21b.

Figure 6:
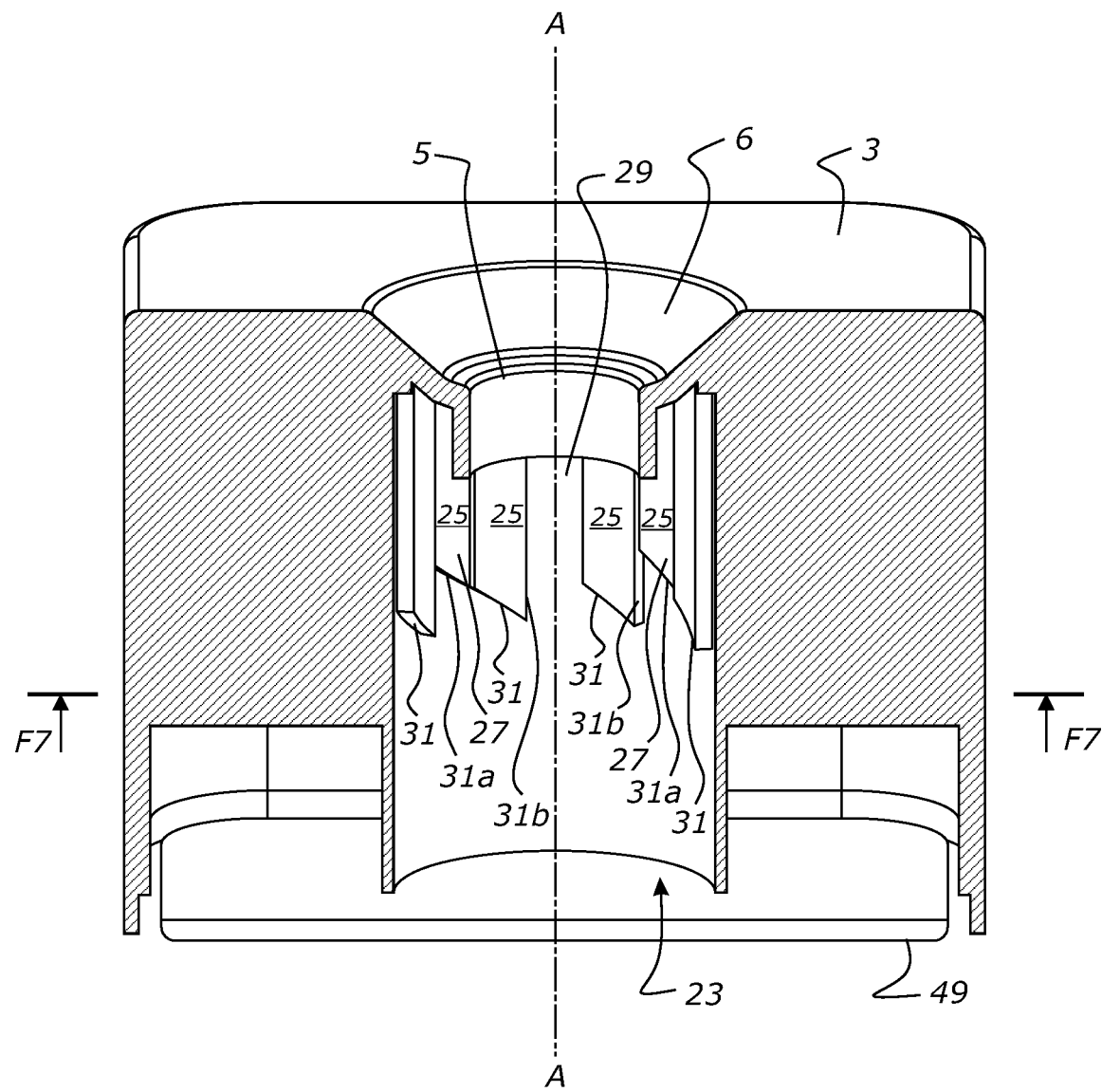
FIG. 6 is a front perspective section view of the housing of the apparatus shown in FIGS. 1 and 2.
Figure 7:
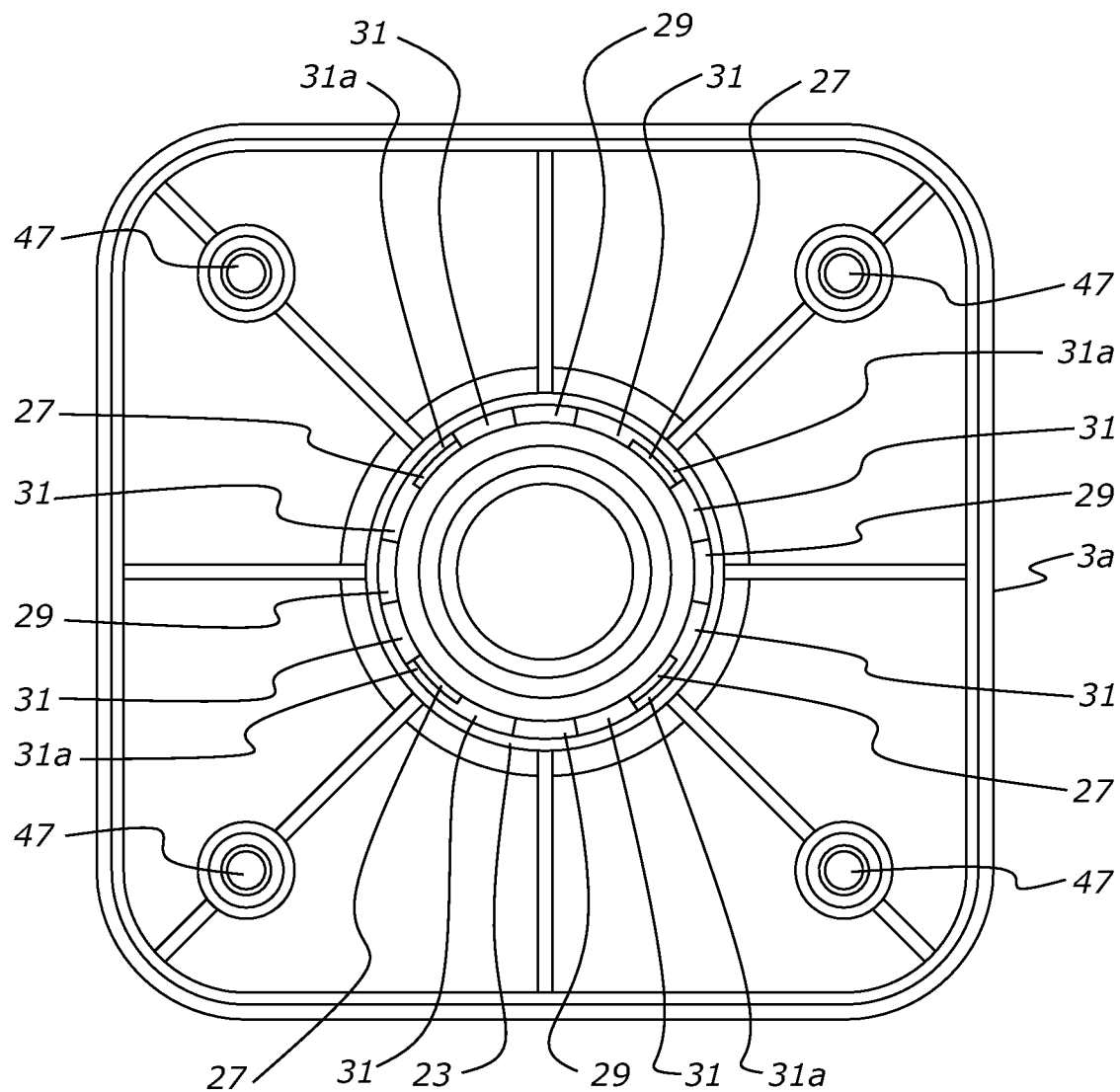
FIG. 7 is an underside plan section view of the housing of the apparatus shown in FIGS. 1 and 2, through line F7 shown in FIG. 6.

As can be seen in FIGS. 6 and 7, the housing 3 comprises a bore 23 for housing the clamp 7, cam member 9, and ratchet member 11. The diameter of the bore 23 is wider than the diameter of the aperture 5 for receiving the needle sheath.

The bore 23 of the housing 3 comprises a plurality of inward projections 25. These projections define four shallow vertical guide grooves 27, four deeper vertical grooves 29, and eight angled cam surfaces 31.

The guide projections 17 on the cam member 9 are received in the vertical grooves 27, 29 in the housing 3. The guide projections 17 are slidable up and down in the grooves 27, 29 to enable axial and non-rotating movement of the cam member 9 relative to the housing 3.

The ratchet member 11 is positioned directly below the cam member 9. The housing cam surfaces 31 are all angled in the same direction and configured to contact the secondary teeth 21 on the ratchet member 11. The spring 33 or other biasing device biases the ratchet member 11 upwards relative to the base 3b of the housing 3, urging the primary teeth 19 into contact with the cam member cam projections 13 and/or the secondary teeth 21 into contact with the housing cam surfaces 31.

Four of the housing cam surfaces 31 comprise an extended surface 31a at the base a respective guide groove 27. The other four cam surfaces 31 terminate at the deeper grooves 29. The deeper grooves 29 are configured to receive the secondary teeth 21.

The push mechanism (9, 11, 33, 25) is an indexed mechanism and operates in a similar manner to a push-type mechanism for extending and retracting a ball point pen.

In a first configuration of the mechanism, the ratchet member 11 is in a first position with a peripheral portion of its secondary teeth surfaces 21a contacting the extended portions 31a of the housing cam surfaces 31. The extended cam surface portions 31a prevent the secondary teeth 21 entering the guide grooves 27, which are too shallow to receive the secondary teeth.

The angled surfaces 31a, 21a of the secondary teeth 21 and housing cam surfaces 31, and the ratchet member spring 33, urge the ratchet member 21 anticlockwise (when viewed from above) about the axis A. However, the vertical surfaces 21b on the secondary teeth 21 contact respective vertical surfaces 31b on the housing projections 25 to prevent rotation of the ratchet member about the axis A.

In this position, the cam projections 13 on the cam member 9 and the primary teeth 19 on the ratchet member are rotationally offset such that the apexes 13a of the cam member cam projections 13 are positioned over a midpoint of an angled surface 19a of the respective primary tooth.

From the first position, pushing the cam member 9 downwards causes the ratchet member 11 to also move downwards. The ratchet member 11 will move down with the cam member 9, with the apexes 13a of the cam member cam projections 12 contacting the respective primary tooth angled surface 19a, until the length of the vertical surfaces 21b on the secondary teeth 21 are positioned below the vertical surfaces 31b on the housing projections.

The primary teeth 19 on the ratchet member, along with the spring 33, then urge the ratchet member 11 anticlockwise about the axis A and upwards relative to the cam member 9 until the apexes 13a of the cam member projections 13 are positioned in respective bases 19b of the primary teeth 19.

When the downwards force on the cam member 9 is released, the ratchet spring 33 pushes the ratchet member 11 upwards so that the secondary teeth 21 contact the next housing cam surface 31. The housing cam surfaces 31, the angled surfaces 21a of the secondary teeth 21, and the ratchet member spring 33, again urge the ratchet member 11 anticlockwise about the axis A. From this position, the angled housing cam surfaces 31 terminate at the deeper teeth grooves 29. Therefore, as the ratchet member 11 is turned, the secondary teeth 21 enter the teeth grooves 29 in the housing.

When the secondary teeth 21 enter the grooves 29, the ratchet spring 33 forces the ratchet member 11 upwards to a second position. In this second position, the ratchet and cam members 9, 11 are positioned higher than in the first mechanism configuration, and the grooves 29 prevent rotation of the ratchet member 11.

Figure 8:
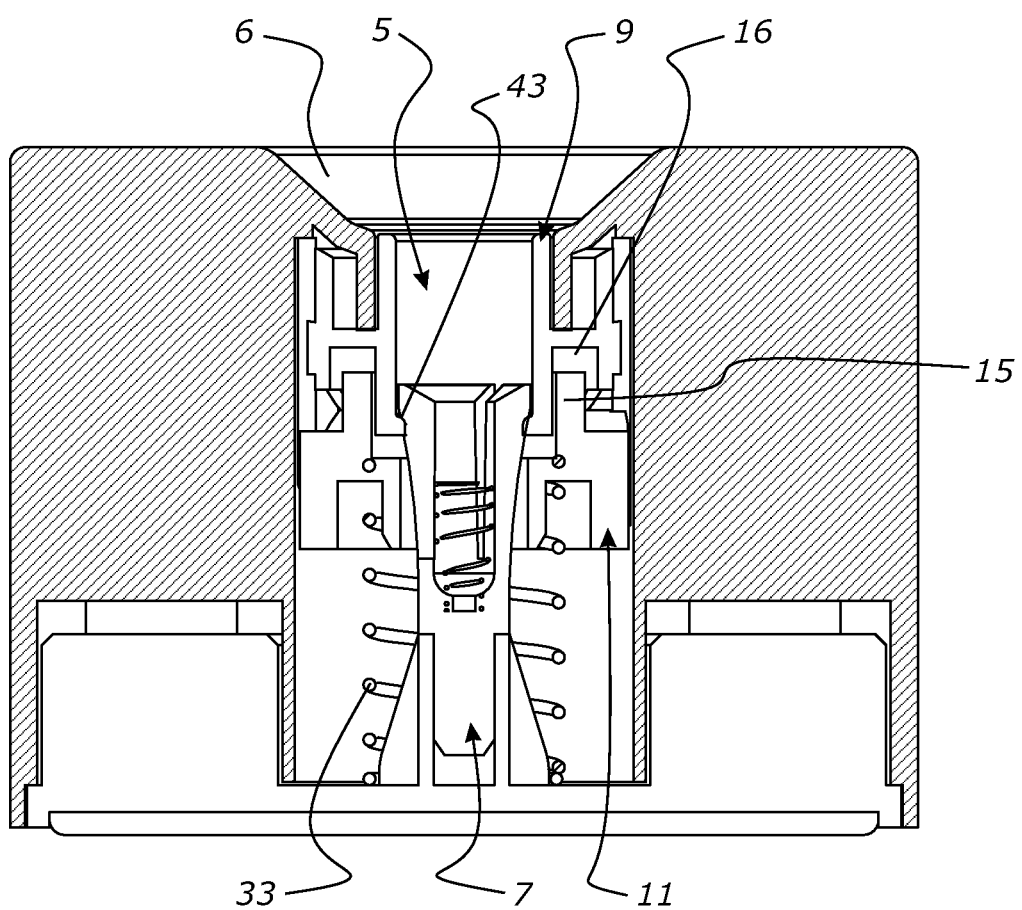
FIG. 8 is a section view of the apparatus of FIGS. 1 and 2 in a clamped configuration.

In this second mechanism configuration, upwards movement of the cam member 9 is limited by the housing shell 3a, and upwards movement of the ratchet member 11 is limited by the cam member 9. A portion of the ratchet collar 15 is received by a recess 16 in the cam member 9 (FIG. 8).

From the second position, pushing the cam member 9 downwards again causes the ratchet member 11 to also move downwards until the vertical surfaces 21b on the secondary teeth 21 clear the respective vertical surfaces 31b on the housing projections. The primary teeth 16 on the ratchet member 11 and the spring 33 then urge the ratchet member 11 anticlockwise about the axis A and upwards relative to the cam member 9, until the apexes 13a of the cam member projections 13 are positioned in respective base 19b of the primary teeth 19.

When the downwards force on the cam member 9 is released, the ratchet spring 33 again pushes the ratchet member 11 upwards so that the secondary teeth 21 contact the housing cam surface 31. The angled surfaces 31, 21a of the housing cam surfaces 31 and secondary teeth 21, and the ratchet member spring 33, again urge the ratchet member 21 anticlockwise about the axis A relative to the cam member 7 and the housing 3, returning the ratchet member 11 to the first position with the ratchet secondary teeth surfaces 21a contacting the extended portions 31a of the cam surfaces 31. The vertical surfaces 21b on the secondary teeth 21 contact respective vertical surfaces 31b on the housing projections to prevent rotation of the ratchet member 11.

In the process of moving from the first position to the second position, and back to the first position, the ratchet member 11 rotates through 90 degrees, or a quarter turn, about the axis A. In the second position, the ratchet member is rotated 45 degrees from its orientation in the first position.

The radial clamp 7 comprises a base 35 and three resilient fingers 37 extending upwards from the base. The base 35 is shown as cylindrical, but may have other shapes, and is seated in a complementary boss 41 in the housing base 3b.

The fingers 37 define a cylindrical recess 39 for receiving a needle sheath. The fingers 37 preferably comprise a resilient material such that they can be pushed inwards or outwards and return to a neutral position when the force is released. The fingers 37, or outer surfaces of the fingers, taper or project outwards towards the top of the clamp 7 such that an outer diameter D1 of the clamp 7 is greater at a top of the fingers than the outer diameter D2 at the base of the fingers.

In the embodiment shown, in the neutral clamp position the clamp 7 is open and the diameter of the cylindrical recess 39 is sufficient to receive a needle sheath.

The fingers 37 of the clamp 7 are positioned inside the ratchet member collar 15. As the ratchet member 11 moves between the first and second positions, it moves up and down relative to the clamp 7.

In the first configuration of the push mechanism, the ratchet member 11 and cam member 9 are positioned at a lower, narrower part of the clamp. In this position, the clamp fingers 37 are in their neutral position for receiving or releasing a needle sheath (FIG. 10(*i*)).

In the second configuration of the push mechanism, the ratchet member 11 and cam member 9 are positioned towards the wider top of the clamp 7. In this position an inner surface or lip 43 of the cam member 9, positioned above the ratchet 15, bears against the fingers 37 of the clamp 7, pushing the fingers 37 inwards to a clamping position for gripping a needle sheath (FIG. 8 and FIG. 10(*iii*)). Alternatively, or additionally, an inner smaller diameter surface 16 of the ratchet collar 15 may bear against the fingers 37 of the clamp 7, pushing the fingers inwards to a clamping position for gripping a needle sheath.

Figure 9:
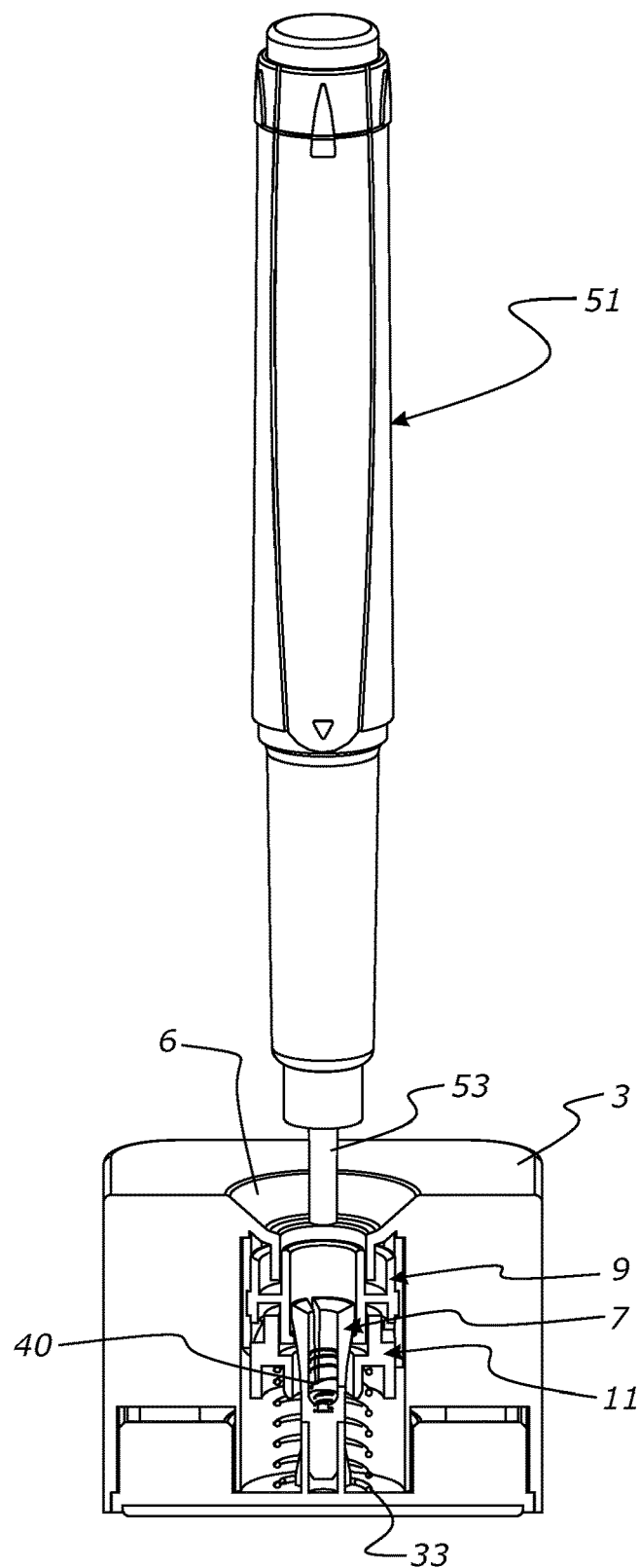
FIG. 9 is a perspective section view of the apparatus of FIGS. 1 to 8, in an unclamped configuration, and a sheathed injection pen for insertion into the apparatus.
Figure 10:
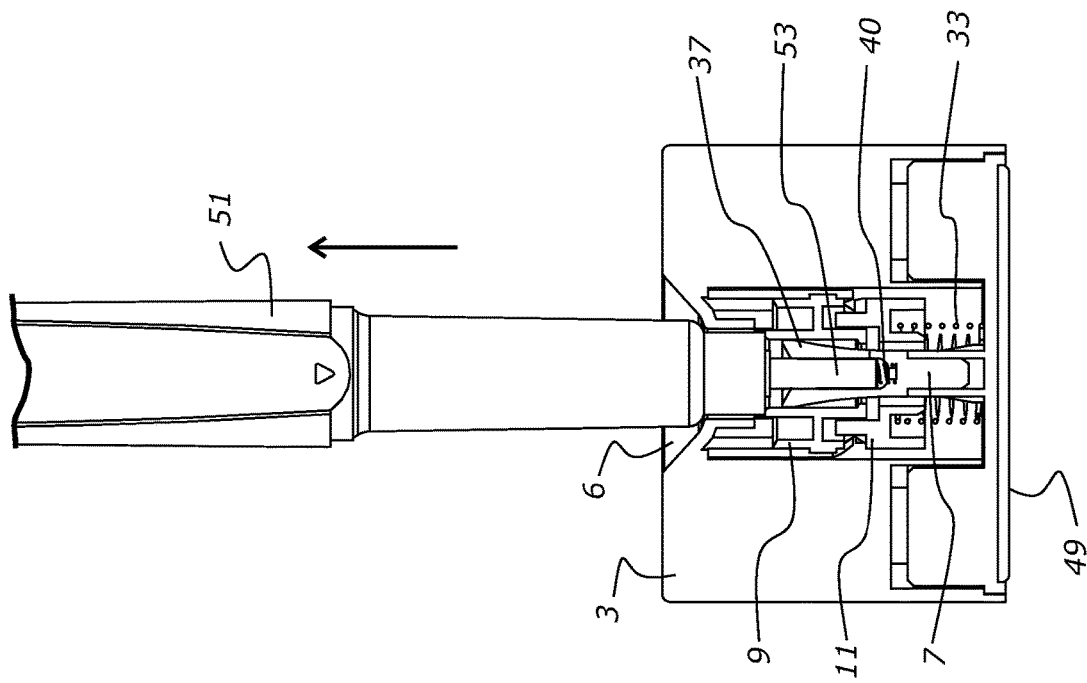
FIGS. 10(*i*) to 10(*iv*) are front section views showing step-by-step operation of the apparatus of FIGS. 1 to 8, where FIG. 10(*i*) shows the apparatus in an unclamped configuration for receipt of the needle sheath, FIG. 10(*ii*) shows the apparatus in an intermediate configuration with the needle sheath pressed into the clamp, FIG. 10(*iii*) shows the apparatus in a clamped configuration holding the needle sheath with the needle lifted out of the apparatus, and FIG. 10 (*iv*) shows the apparatus in the intermediate position, with the needle pressed back into the sheath to resheath the needle.

FIGS. 9 and 10(*i*) to 10(*iv*) illustrate the step-by-step operation of the apparatus 1 for removing a sheath 53 from an injection pen 51. FIGS. 9 and 10(*i*) show a sheathed injection pen 51 poised above the apparatus 1. From this position, the pen 51 is pushed downwards along the axis A, moving the needle sheath 53 through the housing aperture 5. A chamfer 6 around the housing aperture 5 helps to guide the sheath 53 into the aperture 5 if the pen 51 is not correctly aligned.

As the pen 51 is pushed down, the needle end 52 of the pen body contacts a top surface 10 of the cam member 9. This, in turn, pushes the cam member 9 and ratchet member 11 downwards to an intermediate position shown in FIG. 10(*ii*), thereby operating the push-mechanism as described above. When the needle end 52 of the pen body is contacting the top surface 10 of the cam member, the needle sheath 53 is positioned towards the base of the clamp recess 39 and a clamp spring 40 (described below) is compressed.

From the intermediate position, when the push force is released from the pen 51 by lifting the pen from the apparatus 1, the mechanism moves into its second configuration to clamp the needle sheath.

A biasing device in the form of a spring 40 is positioned in the clamp recess 39, at the base of the recess. This spring 39 biases the needle sheath 53 back towards the top of the clamp 7. As the sheath 53 raises so does the cam member 9. The clamp action only acts once the cam member 9 has risen adequately to move the clamp fingers 37 inwards to clamp the sheath 53. While the needle sheath 53 is held in the clamp 7, the needle 55 can be pulled upwards from the device and unsheathed, leaving the sheath 53 held in the clamp of the apparatus 1, as shown in FIG. 10(*iii*). The biasing device is shown as being a coil spring, but could be in a different form such as a resilient block for example.

To place the sheath 53 or cap back on the needle, a user presses the pen 51 downwards into the apparatus 1 into the position shown in FIG. 10(*iv*). If the needle device 51 has an engagement feature for engaging the sheath 53, this downwards force 'clicks' the sheath 53 back on the needle 55. Alternatively, the sheath 53 may have a friction fit with the needle device 51 and the downwards force presses the sheath 53 back on the needle 55. The needle end 52 of the pen body again contacts a top surface 10 of the cam member 9. This, in turn, pushes the cam member 9 and ratchet member 11 downwards to the intermediate position, to operate the push-mechanism.

From this position, when the push force is released from the pen 51 by lifting the sheathed pen 15 from the apparatus 1, the mechanism returns to the first configuration shown in FIG. 10(*i*), to release the needle sheath 53.

The force required to push the ratchet collar 15 down is greater than the force required to push or 'click' the sheath 53 back on the needle, and the clamping force must be sufficient to remove the sheath 53 from the needle device. The clamping force and the force to push the ratchet collar 15 down are at least in part determined by the size of the spring 33. The apparatus 1 is configured to sit on a flat surface such as a table or bench. The apparatus may comprise a high friction or adhesive surface 49 on the base of the housing. Alternatively, the apparatus 1 may comprise mounts for permanently mounting the apparatus to a table, bench, wall, or other surface.

The described embodiments provide a robust device with few moving parts. The apparatus enables a needle device to easily be unsheathed, by people with limited mobility.

Preferred embodiments of the invention have been described by way of example only and modifications may be made thereto without departing from the scope of the invention.

A number of features are shown in the drawings for assembling the apparatus. For example, the base 3b of the housing is connected to the top shell of the housing 3a by screws 45 and receptacles 47. However, the housing may be otherwise assembled, for example it may be glued. Similarly, the clamp 7 is preferably glued in the boss 41 in the base 3b of the housing. Alternatively the clamp may be otherwise connected to the base.

In an alternative embodiment, the clamp 7 could be movable relative to the base 3b. For example, with a biasing device such as a spring positioned between the clamp and the housing base, so the clamp moves as the needle sheath 53 is pushed down.

The cam member 9 shown comprises eight guide projections 17. Instead of projections, the cam member 9 may comprise other guide features such as recesses, and the housing may comprise guide projections. The cam member 9 may have as few as one guide feature and could comprise more or fewer than eight guide features.

The apparatus 1 shown comprises a quarter turn mechanism, in which the ratchet member turns through 90 degrees between subsequent cycles. Alternatively, the ratchet member may turn through a larger or smaller angle between cycles. For example, the housing 3 may comprise more or fewer teeth slots 29, the ratchet member 11 may comprise more or fewer primary and/or secondary teeth 19, 21. Suitable modifications would be apparent to a person skilled in the art.

The ratchet member 11 may alternatively be configured to turn in a clockwise direction.

The clamp 7 may comprise more or fewer than three finger 37s. In the embodiment shown, the clamp fingers 37 and base 35 are integral. The fingers or other jaw members and base could instead be separate components, with the fingers biased relative to the base. Alternatively the device may comprise a different type of clamp. For example, the clamp may be a radial clamp or may be a non-radial clamp such as a scissor-type clamp.

The mechanism parts may have other arrangements. For example, the ratchet member could be positioned above the cam member. Additionally or alternatively, the mechanism could be configured such that the collar member and cam member are positioned around a shaft and run along tracks on the shaft.

Because the preferred embodiment apparatus does not rely on gravity for its operation, the apparatus could be used on any suitable orientation.

The invention claimed is:

1. An apparatus for unsheathing and resheathing a needle device comprising:
   a housing;
   a cam member that is movable in an axial direction relative to the housing;
   a ratchet member that is rotatable relative to the housing and movable in the axial direction between a first position and a second position upon movement of the cam member; and
   a clamp having at least two jaw members, configured to receive at least a portion of a needle sheath; wherein in the first position of the ratchet member, the jaw members are in an open configuration for receipt or release of the needle sheath, and in the second position of the ratchet member, the ratchet member and/or the cam member holds the jaw members in a gripping position for gripping the needle sheath.

2. The apparatus according to claim 1, wherein the cam member is movable relative to the clamp in the axial direction, and wherein in the gripping position of the clamp, an inner surface of the cam member holds the jaw members inwards.

3. The apparatus according to claim 1, wherein the cam member and ratchet member each comprise a collar, and the collars extend around a portion of the clamp.

4. The apparatus according to claim 1, wherein the ratchet member is biased in the axial direction, toward an aperture in the housing for receipt of the needle sheath.

5. The apparatus according to claim 1, wherein the cam member comprises at least one guide slidably engaged with the housing.

6. The apparatus according to claim 1, wherein the clamp is configured to apply a radial clamping force.

7. The apparatus according to claim 1, wherein the jaw members define a recess for receiving the needle sheath, and a biasing device is provided at the base of the recess for biasing the needle sheath away from the base of the recess.

8. A method of unsheathing a sheathed needle device comprising pressing the sheathed needle device into the apparatus according to claim 1 such that the clamp grips the sheath, and lifting the needle device from the apparatus, wherein the sheath remains in the clamp.

9. A method of sheathing an unsheathed needle using the apparatus according to claim 1, wherein the clamp of the apparatus grips a sheath, the method comprising pressing the needle device into the sheath to attach the sheath to the needle device, and lifting the needle device from the apparatus such that the clamp releases the sheath.

10. The apparatus according to claim 4, wherein the ratchet member comprises a plurality of angled primary teeth, with the cam member having at least one angled cam surface configured to engage the primary teeth on the cam member.

11. The apparatus according to claim 10, wherein the ratchet member further comprises at least one secondary tooth and the housing comprises a plurality of angled cam surfaces configured to turn the ratchet member to allow the secondary tooth to enter a complementary tooth slot in the housing.

12. The apparatus according to claim 11, wherein in the first position of the collar or a first position of the ratchet member, the secondary ratchet teeth are configured to be positioned on the angled cam surfaces on the housing; and in the second position of the collar or a second position of the ratchet member, the secondary ratchet teeth are configured to be positioned in a respective housing slot.

13. The apparatus according to claim 11, wherein the cam surfaces and slots on the housing are configured to turn the ratchet member through 45 degrees as it moves between the first position of the collar or ratchet member and the second position of the collar or ratchet member.

14. An apparatus for unsheathing and resheathing a needle device comprising:
   a housing;
   a clamp having at least two jaw members, configured to receive at least a portion of a needle sheath;
   a collar positioned around the clamp and movable in an axial direction relative to the clamp and the housing between a first collar position and a second collar position; and
   an indexed push mechanism for moving the collar between the first collar position and second collar position upon application of a push force by the needle device; wherein in the first collar position, the jaw members are in an open configuration for receipt or release of the needle sheath, and in the second collar position, the collar holds the jaw members inwards for gripping the needle sheath.

15. The apparatus according to claim 14, wherein the collar is provided by the indexed push mechanism.

16. The apparatus according to claim 14, wherein the indexed push mechanism comprises a cam member that is movable in an axial direction relative to the housing and a ratchet member that is movable in the axial direction and rotatable relative to the cam member upon movement of the cam member, wherein the collar is provided by the cam member and/or the ratchet member.

17. A method of unsheathing a sheathed needle device comprising pressing the sheathed needle device into the apparatus according to claim 14 such that the clamp grips the sheath, and lifting the needle device from the apparatus, wherein the sheath remains in the clamp.

18. A method of sheathing an unsheathed needle using the apparatus according to claim 14, wherein the clamp of the apparatus grips a sheath, the method comprising pressing the needle device into the sheath to attach the sheath to the needle device, and lifting the needle device from the apparatus such that the clamp releases the sheath.

* * * * *